United States Patent [19]

Campion, Jr.

[11] 4,029,453

[45] June 14, 1977

[54] MOLDING APPARATUS FOR MAKING A DENTAL FLOSS DEVICE WITH FLOSS TENSIONING MEANS

[75] Inventor: James M. Campion, Jr., Minnetonka, Minn.

[73] Assignee: Philmon & Hart Laboratories, Inc., Bloomington, Minn.

[22] Filed: Nov. 4, 1974

[21] Appl. No.: 520,298

[52] U.S. Cl. .......................... 425/111; 425/114; 425/122; 425/126 R; 425/129 R; 264/251; 132/91; 249/97
[51] Int. Cl.² ...................................... B29F 1/00
[58] Field of Search ............... 425/111, 122, 126 R, 425/129 R, 114; 249/95, 97; 264/40, 251, 157; 132/91, 92

[56] References Cited

UNITED STATES PATENTS

| | | | |
|---|---|---|---|
| 1,970,575 | 8/1934 | Reitzel | 132/91 |
| 2,180,522 | 11/1939 | Henne | 132/91 |
| 2,443,415 | 6/1948 | Buscarino | 132/91 |
| 3,097,395 | 7/1963 | Yoshida | 425/129 |
| 3,769,396 | 10/1973 | Espinosa | 264/157 |
| 3,783,883 | 1/1974 | Alexander | 132/91 |
| 3,849,042 | 11/1974 | Anderegg | 425/129 R |
| 3,890,077 | 6/1975 | Holman | 425/111 |
| 3,926,201 | 12/1975 | Katz | 264/157 |

FOREIGN PATENTS OR APPLICATIONS 629,153  9/1949  United Kingdom ............... 425/111

Primary Examiner—Robert L. Spicer, Jr.
Attorney, Agent, or Firm—Wicks & Nemer

[57] ABSTRACT

A method and apparatus for tensioning dental floss is disclosed for use in the molding of a tooth cleaning dental instrument including a bow-shaped member having a first end and a second end with dental floss tensioned between the ends. A suitable plastic-like material injection mold having cavities for the molding of the dental instrument and having line cavities for receiving the dental floss is used in conjunction with the apparatus of the present invention. Dental floss is supplied from suitable sources and directed by guide members to tensioning members including primary and secondary tensioning members. The secondary tensioning members provide supplemental tensioning of the dental floss during the cool down period after the injection of the plastic-like material into the mold. The dental floss is tensioned by primary tensioning members during the injection of the plastic-like material into the mold. Guide members are further provided to direct the dental floss into the line cavities of the mold, and a holding member is provided to hold the end of the dental floss in a stationary position on the opposite side of the mold from the tensioning members.

13 Claims, 4 Drawing Figures

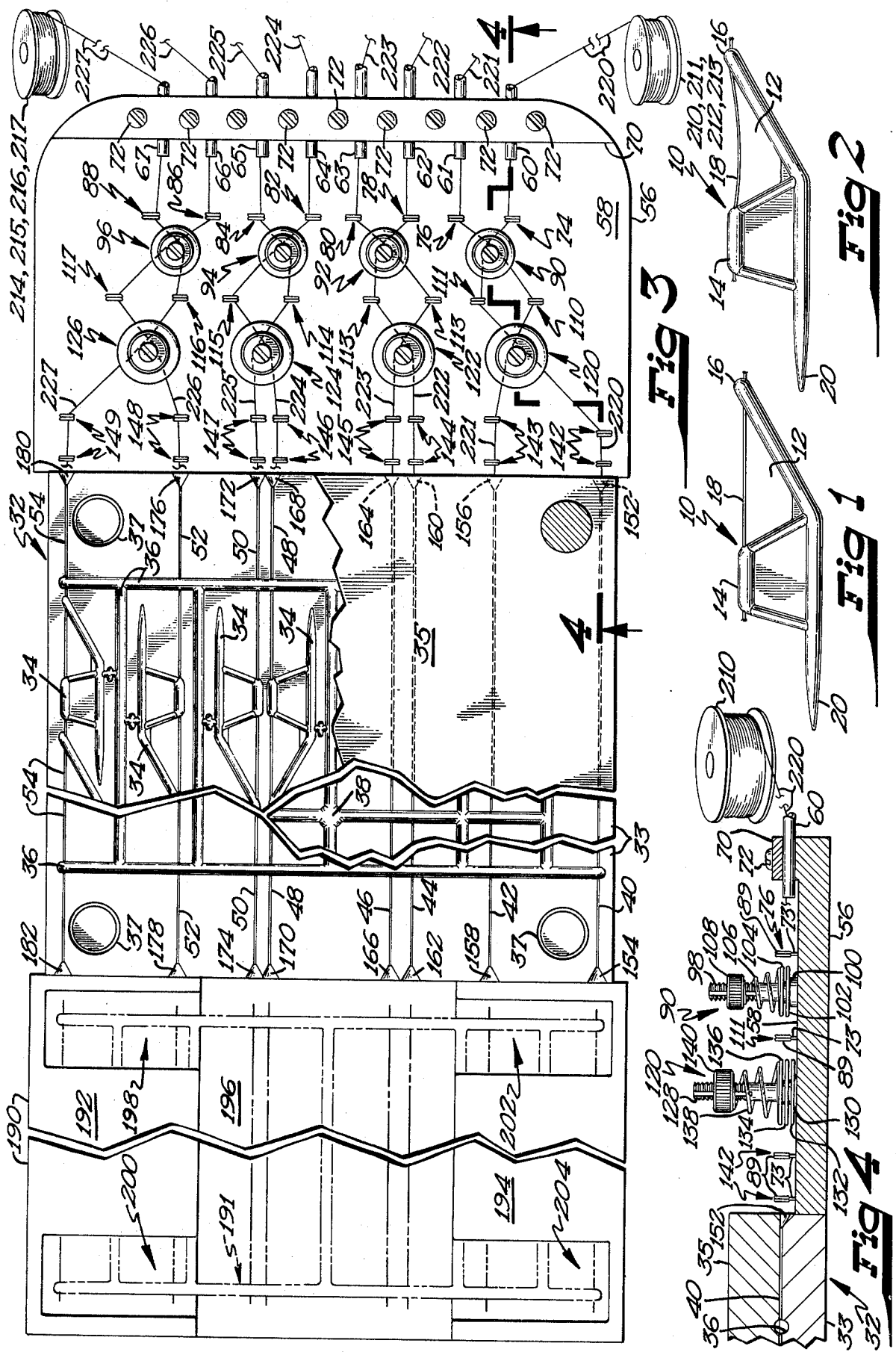

MOLDING APPARATUS FOR MAKING A DENTAL FLOSS DEVICE WITH FLOSS TENSIONING MEANS

BACKGROUND

The present invention relates generally to tensioning dental floss and more specifically to the method and apparatus for tensioning dental floss in a plastic-like material injection mold.

With the increasing public awareness of the need for teeth cleanliness to reduce tooth decay, bad breath, and diseases of the mouth, an increasing need has arisen for instruments to aid in tooth cleaning. The present invention fills such a need.

SUMMARY

In the preferred embodiment, the present invention provides a method and apparatus for producing a simple, low cost tooth cleaning dental instrument including a bow-shaped member having a first end and a second end with dental floss tensioned therebetween. The instruments can be formed in a plastic-like material injection mold having line cavities for receiving the dental floss therein, as follows. Dental floss is supplied from a source, is directed from the source by guiding members, and is advanced through the open mold. The dental floss is further guided into the line cavities of the mold and is held in a stationary position by one end. The dental floss is tensioned by a primary tensioning member to tension the dental floss during the injection of the plastic-like material into the mold. Secondary tensioning members supplementally tension the dental floss to firmly hold the dental floss under static tension during the cool down period after the injection of plastic-like material into the mold.

It is thus an object of the present invention to provide a novel method and apparatus for tensioning dental floss.

It is a further object of the present invention to provide a novel method and apparatus for tensioning dental floss in a mold used in the production of a tooth cleaning dental instrument.

It is a further object of the present invention to provide a novel apparatus for primary and secondary tensioning of dental floss wherein the primary tensioning means firmly holds the dental floss under static tension during the injection of the plastic-like material into the mold and wherein the secondary tensioning means supplementally tensions the dental floss to hold the dental floss under static tension during the cool down period.

These and further objects and advantages of the present invention will become clearer in light of the following detailed description of an illustrative embodiment of the present invention described in connection with the drawings.

DESCRIPTION OF THE DRAWINGS

FIG. 1 shows a tooth cleaning dental instrument which was made according to the teachings of the present invention and has a properly tensioned length of dental floss.

FIG. 2 shows a tooth cleaning dental instrument with an improperly tensioned length of dental floss, illustrating the advantages of the present invention.

FIG. 3 shows a partial side elevational view of an embodiment of apparatus according to the present invention, with some parts of the apparatus being shown broken away.

FIG. 4 shows a cross sectional view of apparatus of FIG. 3 taken according to section lines 4—4 in FIG. 3 with the dental floss removed.

For use in the various figures of the drawings, the same numerals designate the same or similar parts. Furthermore, when the terms "vertical", "horizontal", "front", "back", and similar terms are used herein, it should be understood that these terms have reference only to the structure shown in the drawings as it would appear to a person viewing the drawings and are utilized only to facilitate describing the invention.

DESCRIPTION

In FIGS. 1 and 2, a tooth cleaning dental instrument is shown generally as 10. Instrument 10 can be formed from various plastic-like materials, such as those of the type which can be injected into a mold cavity in liquid or semi-liquid form and will harden in the mold cavity, after injection therein, to form a rigid object having a shape corresponding to that of the mold cavity. After the plastic-like material becomes rigid, it should be sturdy enough to allow it to hold dental floss under tension, strong enough to allow a force to be exerted on the instrument, and pliable enough to prevent instrument 10 from breaking during use. Instrument 10 includes a bow-shaped member 12 hving a first end 14 and a second end 16. A length of dental floss 18 is tensioned between first end 14 and second end 16 of bow-shaped member 12. A handle 20, having a preferred shape similar to that of a toothpick, is used in manipulation of the instrument 10 and can additionally be used as a pick member for cleaning between teeth.

In FIGS. 3 and 4 the apparatus for tensioning dental floss is shown in a preferred form and generally designated 30 for use with a mold 32 for the production of dental instrument 10, as shown in FIGS. 1 and 2. Mold 32 includes a mold right side 33 and a mold left side 35. Alignment pins and holes 37 are provided in side 33 and side 35 of mold 32 to insure the side 33 aligns with side 35 during the closing of mold 32 therefore forming mold cavities 34, as best seen in FIG. 4, having a shape corresponding to that of instrument 10. Flow channels 36 supply plastic-like material to cavities 34 from the plastic-like material inlet 38 in a conventional manner. Mold 32 further includes line cavities 40, 42, 44, 46, 48, 50, 52, and 54 in the right side 33 of mold 32 for receiving dental floss therein. Line cavities 40-54 are arranged such that they pass between the first end 14 and the second end 16 of instrument 10 when instrument 10 is being formed within cavities 34.

Apparatus 30 includes a support plate 56, preferably formed of rigid material such as wood, having a top surface 58. Apparatus 30 further includes tubing 60, 61, 62, 63, 64, 65, 66, and 67 captured between a latching member 70 and top surface 58 of plate 56 by screws 72. Tubing 60–67 guides the dental floss and prevents the dental floss from becoming entangled as will be explained further hereinafter.

Guide members 74, 76, 78, 80, 82, 84, 86, and 88 can optionally be provided to direct the floss from tubing 60–67 as will be explained hereinafter. As best seen in FIG. 4, guide members 74–88 are preferably formed from a nail 73 having a loop portion 89 formed on the upper portion of nail 73 for receiving the dental floss therein. Nail 73 is fastened to support plate 56 by driving it into support plate 56. The dental floss is directed by guide members 74–88 from tubing 60–67 to secondary tensioning members 90, 92, 94, and 96.

As best seen in FIG. 4, secondary tensioning member 90 includes an upstanding member 98, a boss 100, a first stationary member 102, a second member 104 movable towards first stationary member 102, spring 106, and nut 108. Upstanding member 98, such as a bolt as shown, extends through and is upstanding from surface 58 of support plate 56 and is perpendicular to the direction of the path of the dental floss. In the preferred embodiment, first stationary member 102, and second member 104 are vertically arranged and have the preferred form of washers placed around bolt 98, and boss 100 has the preferred form of a tubular spacer placed around the bottom end of bolt 98 adjacent surface 58. Boss 100 rests on surface 58 of support plate 56 and limits the movement of first member 102 vertically downward. Second member 104 is biased towards first member 102 by spring 106 tensioned between second member 104 and nut 108. The tension of spring 106 can be varied by adjustment of nut 108 which is threadably mounted to the upper end of bolt 98. The dental floss can then be located between first member 102 and second member 104 and is wrapped around bolt 98, as best seen in FIG. 3. Therefore, pressure can be placed on the dental floss in a direction perpendicular to the movement path of the dental floss and resistance to movement created by friction between the dental floss and the outer surface of bolt 98.

Secondary tensioning members 92, 94, and 96 are of substantially similar design to that of secondary tensioning member 90.

Guide members 110, 111, 112, 113, 114, 115, 116, and 117, can also optionally be provided to direct the dental floss. Guide members 110–117 are preferably formed similarly to that of guide members 74, 76, 78, 80, 82, 84, 86, and 88. Guide members 110–117 can then be used to direct the dental floss from secondary tensioning members 90–96 to primary tensioning members 120–126.

As best seen in FIG. 4, primary tensioning member 120 includes an upstanding member 128, a boss 130, third stationary member 132, fourth member 134 movable towards a third member 132, fifth member 136 movable towards third member 132 and fourth member 134, spring 138, and nut 140. Upstanding member 128, in its preferred form as a bolt as shown, extends through and is upstanding from surface 58 of support plate 56 and is perpendiculr to the intended movement path of the dental floss. Boss 130 in its preferred form is a tubular spacer located around the bottom end of bolt 128 adjacent surface 58. Third, fourth, and fifth members 132, 134, and 136, respectively, are verticaly arranged with fourth member 134 located between third member 132 and fifth member 136 and have the preferred form of washers placed around bolt 128. Boss 130 then rests upon surface 58 of support plate 56 to limit the movement of third member 132 downward on bolt 128. Fourth member 134 and fifth member 136 are biased towards third stationary member 132 by spring 138 tensioned between fifth member 136 and nut 140. The tension of spring 138 can be adjusted by rotating nut 140 which is threadably mounted on the upper end of bolt 128. Dental floss can then be located between third member 132 and fourth member 134 and/or located between fourth member 134 and fifth member 136, and optionally wrapped around bolt 128 as best seen in FIG. 3, as will be explained further hereinafter. Therefore, pressure can be placed on the dental floss perpendicular to the intended movement path of the dental floss.

Guide members 142, 143, 144, 145, 146, 147, 148, and 149 can also optionally be provided to direct the dental floss. In the preferred embodiment, guide members 142–149 have a preferred form similar to that of guide members 74, 76, 78, 80, 82, 84, 86, and 88, as best seen in FIG. 4. Guide members 142–149 direct the dental floss from primary tensioning members 120–126 to the mold 32.

Guide members 152 and 154 direct the dental floss into line cavity 40 of mold 32. In their preferred form, members 152 and 154 are notches formed on line cavity 40 adjacent the edges of right side 33 of mold 32, as best seen in FIG. 4. Guide members 156 and 158, 160 and 162, 164 and 166, 168 and 170, 172 and 174, 176 and 178, and 180 and 182 then direct dental floss into line cavities 42, 44, 46, 48, 50, 52, and 54, respectively, in a similar manner.

Located on the opposite end of mold 32 from support plate 56 is a holding member 190. Holding member 190 includes a top portion 192, a bottom portion 194, and an open center section 196. Top portion 192 includes a flattened U-shaped slot having slot ends 198 and 200. Similarly, bottom portion 194 contains a flattened U-shaped slot having slot ends 202 and 204. U-shaped slots of holding member 190 slidably receive the mold product 191 as shown in FIG. 3, in a manner and for a purpose which will be explained hereinafter. Mold product 191 includes rigid plastic-like material formed within cavities 34 of mold 32. It should be noted that the dental floss is embedded and set within the rigid plastic-like material wherever the cavities 34 and channels 36 cross with line cavities 40-54.

Sources 210, 211, 212, 213, 214, 215, 216, and 217, such as spools as shown, supply dental floss 220, 221, 222, 223, 224, 225, 226, and 227, respectively, to apparatus 30.

Dental floss 220 is supplied from source 210 and is guided by tubing 60 to guide member 74. It should be noted that tubing 60 also prevents floss 220 from becoming entangled with floss 221–227 of sources 211–217, respectively.

Floss 220 is then further guided by guide member 74 from tubing 60 to secondary tensioning member 90. Secondary tensioning member 90 together with primary tensioning member 120 prevents floss 220 from losing tensioning during the cool down period as will be explained further hereinafter. Floss 220 is then, in the preferred embodiment shown, wrapped around bolt 98 and is located between first member 102 and second member 104 of tensioning member 90. Therefore, floss 220 is subjected to resistance to movement created by the pressure from spring 106 and the friction of floss 220 against the outer surface of bolt 98. The pressure applied to floss 220 by secondary tensioning member 90 can be adjusted by rotating nut 108 on bolt 98. Therefore, as floss 220 is being advanced through secondary tensioning member 90, a force sufficient to overcome the resistance created by the pressure and friction from secondary tensioning member 90 on floss 220 is required.

Guide member 111 next directs floss 220 from secondary tensioning member 90 to primary tensioning member 120. Primary tensioning member 120 holds floss 220 firmly to prevent floss 220 from losing tension during injection of the plastic-like material into mold 32, as will be explained further hereinafter. Floss 220 is located between third member 132 and fourth member 134 and therefore is subjected to pressure from spring 138. Floss 220 can optionally be wrapped around bolt 128, as best seen in FIG. 3, thus subjecting floss 220 to resistance created by the friction between floss 220 and the outer surface of bolt 128. The pressure applied to floss 220 by primary tensioning member 120 can be adjusted by rotating nut 140 on bolt 128. Therefore, as floss 220 is being advanced through primary tensioning member 120, a force sufficient to overcome the resistance created by pressure and friction from primary tensioning member 120 is also required.

Therefore, the total force required to advance floss 220 is related to the resistance created by primary tensioning member 120 and secondary tensioning member 90.

Floss 220 is then guided from primary tensioning member 120 to guide member 152 by guide members 142. Guide members 152 and 154 direct floss 220 into line cavity 40 of mold 32. The end of floss 220 is held by holding member 190 since floss 220 is embedded in the previous mold product 191 which is held within the U-shaped slot of holding member 190.

In a similar manner, floss 221 is supplied from source 211 and guided by tubing 61 to guide member 76. Tubing 61 also prevents floss 221 from becoming entangled with floss 220 and floss 222–227. Guide member 76 then directs floss 221 from tubing 61 to secondary tensioning member 90. Secondary tensioning member 90 prevents floss 221 from losing tension during the cool down period, as further explained hereinafter. Floss 221 is wrapped around bolt 98 and is located between first member 102 and second member 104 and crosses with floss 220 therebetween. Pressure is applied to floss 221 by spring 106, which can be adjusted by rotating nut 108 on bolt 98. Floss 221 is further subjected to resistance to movement created by the friction between floss 221 and bolt 98. Therefore, as floss 221 is being advanced through secondary tensioning member 90, a force sufficient to overcome the resistance created by the pressure and friction from secondary tensioning 90 is required.

Guide member 110 next directs floss 221 from secondary tensioning member 90 to primary tensioning member 120. Primary tensioning member 120 holds floss 221 firmly to prevent floss 221 from losing tension during injection of the plastic-like material into the mold 32, as will be explained further hereinafter. Floss 221 is wrapped around bolt 128 and is located between fourth member 134 and fifth member 136. Floss 221 is therefore subjected to resistance to movement created by pressure from spring 138 and friction of floss 221 against the outer surface of bolt 128. The pressure applied to floss 221 by primary tensioning member 120 can be adjusted by rotating nut 140 on bolt 128. Therefore, as floss 221 is being advanced through primary tensioning member 120, a force sufficient to overcome the resistance created by the pressure and friction from primary tensioning member 120 is required.

Therefore, the total force required to advance floss 221 is related to the resistances created by primary tensioning member 120 and secondary tensioning member 90.

Floss 221 is then directed from primary tensioning member 120 to guide member 156 by guide members 143. Guide members 156 and 158 direct floss 221 into line cavity 42 of mold 32. The end of floss 221 is held by holding member 190 since floss 221 is located in the previous mold product 191 which is embedded within the U-shaped slot of holding member 190.

It has been found, for best results, that floss 220 should cross with floss 221 within secondary tensioning member 90 and floss 220 should not come in contact with floss 221 in primary tensioning member 120. This is accomplished by having floss 220 and floss 221 located between first member 102 and second member 104 of the secondary tensioning member 90; however, in primary tensioning member 120, floss 220 is located between third member 132 and fourth member 134 of primary tensioning member 120, and floss 221 is located between fourth member 134 and fifth member 136. Further, since floss 220 is located between third member 132 and fourth member 134 and floss 221 is located between fourth member 134 and fifth member 136, more tension can be placed on floss 220 and 221 in primary tensioning member than when both floss 220 and 221 are located between first member 102 and 104 as shown in secondary tension member 90.

In a similar manner, floss 222 is supplied from source 212 and passes through tubing 62, guide member 78, secondary tensioning member 92, guide member 113, primary tensioning member 122, guide members 144 and into guide members 160 and 162 which direct floss 222 into line cavity 44 of mold 32.

In a similar manner, floss 223 is supplied from source 213 and passes through tubing 63, guide member 80, secondary tensioning member 92, guide member 112, primary tensioning member 122, guide members 145 and into guide members 164 and 166 which direct floss 223 into line cavity 46 of mold 32.

In a similar manner, floss 224 is supplied from source 214 and passes through tubing 64, guide member 82, secondary tensioning member 94, guide member 115, primary tensioning member 124, guide members 146 and into guide members 168 and 170 which direct floss 224 into line cavity 48 of mold 32.

In a similar manner, floss 225 is supplied from source 215 and passes through tubing 65, guide member 84, secondary tensioning member 94, guide member 114, primary tensioning member 124, guide members 147, and into guide members 172 and 174 which direct floss 225 into line cavity 50 of mold 32.

In a similar manner, floss 226 is supplied from source 216 and passes through tubing 66, guide member 86, secondary tensioning member 96, guide member 117, primary tensioning member 126, guide members 148, and into guide members 176 and 178 which direct floss 226 into line cavity 52 of mold 32.

In a similar manner, floss 227 is supplied from source 217 and passes through tubing 67, guide member 88, secondary tensioning member 96, guide member 116, primary tensioning member 126, guide members 149, and into guide members 180 and 182 which direct floss 227 into line cavity 54 of mold 32.

OPERATION

The method of tensioning dental floss 220–227 for production of dental instrument 10 through the use of apparatus 30 of the present invention can now be explained. It should be noted that, as the plastic-like material used to fabricate the dental instruments 10 cool, the plastic-like material has been found to become smaller or shrink. Thus, as the plastic-like material cools within cavity 34 of mold 32, the material shrinks within cavity 34. It has also been found that floss 220-227 supplied to apparatus 30 must be under a sufficient amount of tension to prevent floss 18 from becoming loose within mold 32. Sufficient tension of floss 18 of instrument 10 is required for the span between ends 14 and 16 to allow use of instrument 10 within the mouth. This is of particular importance when the span between the ends 14 and 16 is large, such as in the range of one inch. A span of one and one quarter inches (approximately 3.25 centimeters), is shown in FIGS. 1 and 2, for the preferred embodiment. If floss 220-227 is not firmly held under a static tension in apparatus 30, as the plastic-like material shrinks upon cooling, the floss will be pulled through the tensioning mechanisms and will become loose in the resulting instrument 10, as shown in FIG. 2. If floss 18 does not have enough tension in instrument 10, floss 18 will fray very easily and further instrument 10 will become much more difficult to use in the mouth.

However, if the floss is firmly held under sufficient static tension, dental floss 220-227 slides within the material of ends 14 and 16 of instrument 10 located within cavities 34 of mold 32 during the semi-liquid form of the material such that after the material has shrunk during the cool down period, floss 18 remains tight between ends 14 and 16 of instrument 10 as shown in FIG. 1.

For the sake of example, it will be assumed that mold 32 has just finished a cycle of production and is open. Dental floss 220-227 is supplied from sources 210-217 and is guided from sources 210-217 by tubing 60-67 which also prevents floss 220-227 from entangling. The operator grasps a portion of mold product 291, not shown, located in open mold 32 with his hands and also grasps the mold product 191 located within the holding member 190. The operator then slowly pulls on mold products 191 and 291 located within holding member 190 and mold 32, respectively. Since dental floss 220-227 are set and embedded within mold products 191 and 291, as the operator pulls on mold product 291 located within mold 32 and mold product 191 located within holding member 190, floss 220-227 will advance from the sources 210-217 through mold 32. The operator directs the mold product 291 from mold 32 into slot ends 198 and 202 of U-shaped slot of top portion 192 and bottom portion 194, respectively, of holding member 190. The operator continues to pull the mold product 291 from the mold until the mold product 291 is located outside of mold 32 and entirely within holding member 190 between ends 198, 202, and ends 200, 204. At this time, mold product 191 which was previously located within holding member 190 is located outside thereof. At this time, the dental floss between the mold product 191 located outside of the holding member 190 and the mold product 291 located within the holding member 190 can be cut allowing removal and packing of mold product 191 for processing.

As previously explained, since floss 220-227 are located within and captured within mold product 191, holding member 190 holds the end of dental floss 220-227 in a stationary position during the closing of mold 32 and the injecting of the plastic-like material into the cavities 34 of mold 32.

Guide members 152 and 154, 156 and 158, 160 and 162, 164 and 166, 168 and 170, 172 and 174, 176 and 178, and 180 and 182 then direct dental floss 220, 221, 222, 223, 224, 225, 226, and 227 into line cavities 40, 42, 44, 46, 48, 50, 52, and 54, respectively, of mold 32, as explained in detail.

As dental floss 220-227 is being advanced, floss 220-227 is tensioned by primary tensioning members 120-126 together with secondary tensioning members 90-96. Primary tensioning members 120-126 tension the dental floss such that during the injection of the plastic-like material into cavities 34 of mold 32, floss 220-227 is firmly held to prevent floss 220-227 from losing tension. Since dental floss 220-227 is located between third member 132 and fourth member 134 or between fourth member 134 and fifth member 136, floss 220-227 is subjected to pressure from spring 138 biased against fourth member 134 and fifth member 136 toward third member 132. The pressure applied to floss 220-227 can be adjusted by rotating nut 140 threadably mounted on bolt 128. Floss 220-227 can further be subjected to resistance to movement created by friction between floss 220-227 and the outer surfaces of bolts 128 of primary tensioning members 120-126. The amount of friction between floss 220-227 and bolt 128 can be adjusted by varying the angle of wrap of floss 220-227 around bolt 128, for example, by moving guide members 110-117 and/or guide members 142-149, or by additional wraps. Therefore, as floss 220-227 is being advanced through primary tensioning members 120-126, a force sufficient to overcome the resistance created by the pressure and friction on floss 220-227 created by primary tensioning members 120-126 is required. Therefore, floss 220-227 is tensioned as it is being advanced through primary tensioning members 120-126 and are firmly held under static tension between holding member 190 and primary tensioning members 120-126 during injection of the hot plastic-like material into cavities 34 of mold 32.

Secondary tensioning members 90-96 tension dental floss 220-227 such that during the cool down period of the plastic-like material, floss 220-227 is firmly held under static tension to prevent floss 220-227 from becoming loose. Since dental floss 220-227 is located between first member 102 and second member 104 of secondary tensioning members 90-96, floss 220-227 is subjected to pressure in a direction perpendicular to the intended movement path of floss 220-227, from spring 106 biased against second member 104 toward first member 102. The pressure applied to floss 220-227 by secondary tensioning members 90-96 can be adjusted by rotating nut 108 threadably mounted on bolt 98. Floss 220-227 is further subjected to resistance to movement created by friction between floss 220-227 and the outer surfaces of bolts 98 of secondary tensioning members 90-96. The amount of friction between floss 220-227 and bolt 98 can then be adjusted by varying the angle of wrap of floss 220-227 around bolt 98. Therefore, as floss 220-227 is being advanced through secondry tensioning members 90-96, a force sufficient to overcome the resistance created by the pressure and friction on floss 220-227 by secondary tensioning members 90-96 is required. Therefore, floss 220-227 is tensioned as it is being advanced through secondary members 90-96 and are firmly held under static tension between holding member 190 and primary and secondary tensioning members 120-126 and 90-96, respectively, during the cool down period of the hot plastic-like material in cavities 34 of mold 32.

Therefore, the force required to advance floss 220–227 through mold 32 and the amount of static tension under which dental floss 220–227 is held within mold 32 are related to the resistances created by primary tensioning members 120–126 and secondary tensioning members 90–96. It should be noted that the force required for advancement of floss 220–227 through tensioning members 90–96 and 120–126 must be less than the tensional strength of floss 220–227, otherwise floss 220–227 will fray and/or break during advancement thereof.

After mold product 291 which was previously located within mold 32 is located entirely within holding member 190 between ends 198, 202 and ends 200, 204 such that floss 220–227 has advanced through mold 32, left half 35 is moved towards right half 33 of mold 32 thus closing mold 32 such that plastic-like material can be injected into inlet 38 of mold 32. The plastic-like material is then injected into inlet 38 and flows through flow channels 36 into cavities 34. While the plastic-like material flows into cavities 34, dental floss 220–227 is firmly tensioned by primary tensioning members 120–126 to prevent dental floss 220–227 from becoming loose in mold 32 during injection of the plastic-like material into mold 32. After the plastic-like material has been injected into cavities 34 of mold 32, the plastic-like material is allowed to cool therein. During the cooling thereof, the plastic-like material decreases in size. As the plastic-like material shrinks, dental floss 220–227 is firmly held under static tension by secondary tensioning members 90–96 together with primary tensioning member 120–126. As a result, the plastic-like material in a semi-liquid state, located within ends 14 and 16 of instrument 10 located within cavity 34 slips on dental floss 220–227. If floss 220–227 was sufficiently tensioned within mold 32 by primary tensioning members 120–126 and secondary tensioning members 90–96, floss 18 will be tensioned within the resulting instrument 10 as shown in FIG. 1. However, if floss 220–227 is insufficiently tensioned within mold 32, dental floss 220–227 will slip within the tensioning means and therefore as the plastic-like material shrinks, the plastic-like material located within ends 14 and 16 of instrument 10 located within cavity 34 of mold 32 will not slide on dental floss 220–227 and therefore dental floss 18 will become loose between ends 14 and 16 of the resulting instrument 10, as shown in FIG. 2.

It has been found that a single tensioning member will not firmly hold the dental floss under a sufficient static tension. If the single tensioning member is tightened such that a sufficient static tension is placed on the dental floss, the dental floss will break or fray during the advancement thereof through the mold after a cycle of production. However, if the single tensioning member is adjusted to allow advancement of the dental floss without breakage, the dental floss is not firmly held under sufficient static tension during the injection of the plastic-like material into the mold and/or during the cool down period after the injection of the material into the mold.

The amount of tension required will vary with several factors including the temperature of the plastic-like material during injection, the location of the cavities from the inlet of the mold, the type of plastic-like material used, the type of floss used, and other similar factors. Therefore, no predetermined adjustment of tension can be found before operation of the device, but the amount of resistance placed on floss 220–227 is determined by observing the operation of the mold production.

For example, if it appears that the floss is not firmly held during injection of the plastic-like material, it is necessary to tighten the primary tensioning member. However, if it appears that the floss is firmly held during the injection of the plastic-like material into the mold but loses tension during the cool down period, it is necessary to tighten the secondary tensioning member. Further, if the floss should fray or break during advancement thereof, it will be necessary to reduce the pressure exerted by primary tensioning member and/or secondary tensioning member.

It has been found that for best results the floss used in apparatus of the present invention should be of the non-waxed, braided, nylon type such as that sold by Belding Corticelli of New York. Dental floss of the waxed variety and the silk variety will tend to melt within the mold resulting in an instrument 10 in which floss 18 is either broken or unable to withstand the force exerted during use. Floss of the non-braided type has been found to fray more easily than that of the braided type and therefore the braided floss can be placed under a greater tension than the nonbraided floss in apparatus 30 such that floss 18 of instrument 10 is able to withstand a larger force than if nonbraided floss was used.

Now that the basic teachings of the present invention have been explained, many extensions and variations will be obvious to one having ordinary skill in the art. For example, advancement of floss 220–227 could be accomplished by a suitable automatic mechanism.

Additionally, mold 32 could optionally include cutting members for cutting the floss between instruments 10 after the cool down period of the plastic-like material within cavities 34 of mold 32, for example, immediately before mold 32 opens.

Although, in the preferred embodiment, secondary and primary tensioning members are used to tension floss from two sources, each source of dental floss could be provided with its own set of primary and secondary tensioning members. However, apparatus 30 of the preferred embodiment reduces the amount of parts required and thus maximizes the equipment used. Further, the size of the apparatus is greatly reduced.

Further, the paths of floss 220–227 shown in FIG. 3 are the preferred form of the invention. Variations of the paths of floss 220–227 would now be well known to a person skilled in the art, in view of the teachings of the present invention. Such variations are intended to be within the scope of the appended claims.

Thus, since the invention disclosed herein may be embodied in other specific forms without departing from the spirit or general characteristics thereof, some of which forms have been indicated, the embodiment described herein is to be considered in all respects illustrative and not restrictive. The scope of the invention is indicated by the appended claims rather than by the foregoing description, and all changes which comes within the meaning and range of equivalency of the claims are intended to be embraced therein.

I claim:

1. Apparatus for tensioning dental floss through a mold used in the production of a dental tooth cleaning instrument including a bow-shaped member having a first end and a second end and dental floss tensioned between the first and second ends, the mold being of the plastic-like material injection type including at least one line cavity for receiving the dental floss, comprising in combination: at least one source of dental floss; first means for holding the end of the dental floss; primary means for tensioning the dental floss in the mold during the injection of the plastic-like material into the mold; secondary means for supplementally tensioning the dental floss in the mold during the cool down period after the injection of the plastic-like material into the mold; second means for guiding the dental floss from the source of dental floss to the secondary tensioning means; and third means for guiding the dental floss into the line cavity of the mold for causing the dental floss to travel from the source, to the second means, through the secondary tensioning means, the primary tensioning means, the third means, and the mold, and to the first means.

2. Apparatus of claim 1 wherein the apparatus further comprises: fourth means for guiding the dental floss from the secondary tensioning means to the primary tensioning means and fifth means for guiding the dental floss from the primary tensioning means to the third guiding means.

3. Apparatus of claim 1 wherein the first holding means is located on one end of the mold and the primary tensioning means and the secondry tensioning means are located on the end of the mold opposite to the first holding means.

4. Apparatus of claim 1 wherein the secondary means comprises: a first stationary member; a second member movable towards the first stationary member; the dental floss being located between the first and second members; and sixth means for biasing the second member towards the first stationary member for applying pressure to the dental floss in a direction perpendicular to the intended movement path of the dental floss.

5. Apparatus of claim 1 wherein the third guiding means comprises: notches formed in the mold located on the ends of the line cavity adjacent the edge of the mold.

6. Apparatus of claim 1 wherein the apparatus includes a first and a second source of dental floss; the second guide means includes a guide member for directing dental floss from the first source to the secondary tensioning means and another guide member for directing the dental floss from the second source to the secondary tensioning means; the mold includes a first line cavity and a second line cavity; and the third guide means includes a guide member for directing the dental floss from the first source into the first line cavity and a guide member for directing the dental floss from the second source into the second line cavity.

7. Apparatus of claim 6 wherein the dental floss from the first source crosses with the dental floss of the second source in the secondary tensioning means.

8. Apparatus of claim 6 wherein the apparatus further comprises: fourth means for guiding the dental floss from the secondary tensioning means to the primary tensioning means and means for guiding the dental floss from the primary tensioning means to the third guiding means.

9. Apparatus of claim 8 wherein the fourth guide means includes a guide member for directing the dental floss of the first source from the secondary means to the primary means and a guide member for directing the dental floss of the second source from the secondary means to the primary means and the fifth guide means includes a guide member for directing the dental floss of the first source from the primary tensioning means to the third guide means and another guide member for directing the dental floss of the second source from the primary tensioning means to the third guide means.

10. Apparatus of claim 6 wherein the primary tensioning means comprises a third stationary member; a fourth member movable towards the third stationary member; the dental floss of the first source being positioned between the third and fourth members; a fifth member movable towards the third and fourth member, the dental floss of the second source being positioned between the fourth and fifth members; and means for biasing the fourth member and the fifth member toward the third member.

11. Apparatus of claim 10 wherein the primary means further comprises an upstanding member and wherein the third member, fourth member, and fifth member are placed around the upstanding member and the dental floss is wrapped around the upstanding member creating friction between the outer surface of the upstanding member and the dental floss.

12. Apparatus of claim 1 wherein the primary tensioning means and the secondary tensioning means applying pressure to the dental floss in a direction perpendicular to the intended movement path of the dental floss creating a resistance on the dental floss during advancement thereof.

13. Apparatus of claim 4 wherein the secondary means further comprises an upstanding member and wherein the first member and second member are placed around the upstanding member and the dental floss is wrapped around the upstanding member creating friction between the outer surface of the upstanding member and the dental floss.

* * * * *